US00PP37698P2

(12) United States Plant Patent
Hofmann

(10) Patent No.: US PP37,698 P2
(45) Date of Patent: Sep. 15, 2026

(54) ***NEMESIA* PLANT NAMED 'INNEMPLUHO'**

(50) Latin Name: *Nemesia hybrida*
Varietal Denomination: INNEMPLUHO

(71) Applicant: Silvia Hofmann, Mainz (DE)

(72) Inventor: Silvia Hofmann, Mainz (DE)

(73) Assignee: INNOVAPLANT ZIERPFLANZEN GmbH & Co. KG, Gensingen (DE)

( * ) Notice: Subject to any disclaimer, the term of this patent is extended or adjusted under 35 U.S.C. 154(b) by 0 days.

(21) Appl. No.: 19/435,582

(22) Filed: Dec. 29, 2025

(51) Int. Cl.
*A01H 5/02* (2018.01)
*A01H 6/00* (2018.01)

(52) U.S. Cl.
USPC ..... Plt./458

(58) Field of Classification Search
USPC ..... Plt./458
CPC ..... A01H 5/02; A01H 5/00; A01H 6/00
See application file for complete search history.

(56) References Cited

U.S. PATENT DOCUMENTS

PP22,809 P3 * 6/2012 Tellwright ..... A01H 6/00 Plt./458

* cited by examiner

*Primary Examiner* — June Hwu
(74) *Attorney, Agent, or Firm* — C. Anne Whealy

(57) ABSTRACT

A new and distinct cultivar of *Nemesia* plant named 'INNEMPLUHO', characterized by its compact and upright to somewhat outwardly spreading plant habit; moderately vigorous to vigorous growth habit; freely branching habit; freely flowering habit; long flowering period; fragrant purplish red and light yellow bi-colored flowers; and good container and garden performance.

2 Drawing Sheets

Figure 1:
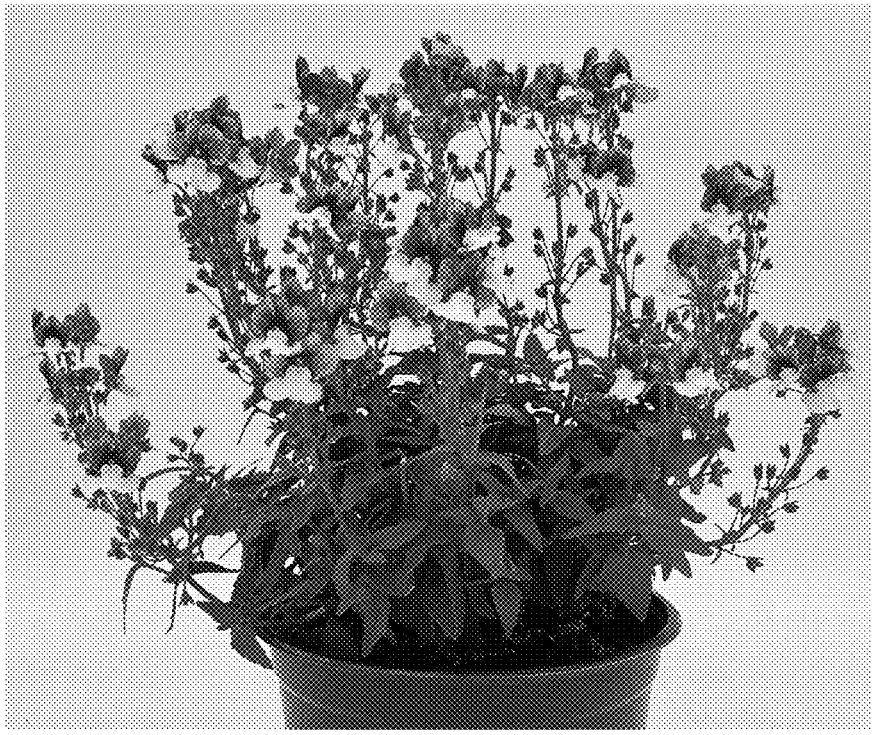

Botanical designation: *Nemesia hybrida.*
Cultivar denomination: 'INNEMPLUHO'.

BACKGROUND OF THE INVENTION

The present invention relates to a new and distinct cultivar of *Nemesia* plant, botanically known as *Nemesia hybrida*, and hereinafter referred to by the name 'INNEMPLUHO'.

The new *Nemesia* plant is a product of a planned breeding program conducted by the Inventor in Heidesheim, Germany. The objective of the breeding program is to create compact and freely branching *Nemesia* plants with good summer garden performance and numerous fragrant bi-colored flowers.

The new *Nemesia* plant originated from a cross-pollination made by the Inventor during the summer of 2021 in Heidesheim, Germany of a proprietary selection of *Nemesia hybrida* identified as code name "purple white", not patented, as the female, or seed, parent with a proprietary selection of *Nemesia hybrida* identified as code number N 15 300-1 tet2, not patented, as the male, or pollen, parent. The new *Nemesia* plant was discovered and selected by the Inventor as a single flowering plant from within the progeny of the stated cross-pollination in a controlled environment in Heidesheim, Germany during the spring of 2022.

Asexual reproduction of the new *Nemesia* plant by terminal vegetative cuttings in a controlled environment in Heidesheim, Germany since the spring of 2023, has shown that the unique features of this new *Nemesia* plant are stable and reproduced true to type in successive generations.

SUMMARY OF THE INVENTION

Plants of the new *Nemesia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INNEMPLUHO'. These characteristics in combination distinguish 'INNEMPLUHO' as a new and distinct *Nemesia* plant:

1. Compact and upright to somewhat outwardly spreading plant habit.
2. Moderately vigorous to vigorous growth habit.
3. Freely branching habit.
4. Freely flowering habit.
5. Long flowering period.
6. Fragrant purplish red and light yellow bi-colored flowers.
7. Good container and garden performance.

Plants of the new *Nemesia* differ primarily from plants of the female parent selection in the following characteristics:

1. Plants of the new *Nemesia* are more compact than plants of the female parent selection.
2. Plants of the new *Nemesia* are more freely branching and denser than plants of the female parent selection.
3. Flowers of plants of the new *Nemesia* are purplish red and light yellow in color whereas flowers of plants of the female parent selection are purple and white in color.
4. Flowers of plants of the new *Nemesia* are sterile whereas flowers of plants of the female parent selection are fertile.

Plants of the new *Nemesia* differ primarily from plants of the male parent selection in the following characteristics:

1. Plants of the new *Nemesia* are more compact than plants of the male parent selection.

2. Plants of the new *Nemesia* are more freely branching and denser than plants of the male parent selection.
3. Flowers of plants of the new *Nemesia* are purplish red and light yellow in color whereas flowers of plants of the male parent selection are cherry pink and light yellow in color.
4. Flowers of plants of the new *Nemesia* are sterile whereas flowers of plants of the male parent selection are fertile.

Plants of the new *Nemesia* can be compared to plants of *Nemesia hybrida* 'Innemvanbe', not patented. In side-by-side comparisons, plants of the new *Nemesia* differ primarily from plants of 'Innemvanbe' in the following characteristics:

1. Plants of the new *Nemesia* are more compact than plants of 'Innemvanbe'.
2. Flowers of plants of the new *Nemesia* are purplish red and light yellow in color whereas flowers of plants of 'Innemvanbe' are violet blue and light yellow in color.

BRIEF DESCRIPTION OF THE PHOTOGRAPHS

The accompanying colored photographs illustrate the overall appearance of the new *Nemesia* plant showing the colors as true as it is reasonably possible to obtain in colored reproductions of this type. Colors in the photographs may differ slightly from the color values cited in the detailed botanical description which accurately describe the colors of the new *Nemesia* plant.

The photograph on the first sheet (FIG. 1) is a side perspective view of a typical flowering plant of 'INNEMPLUHO' grown in a container.

Figure 2:
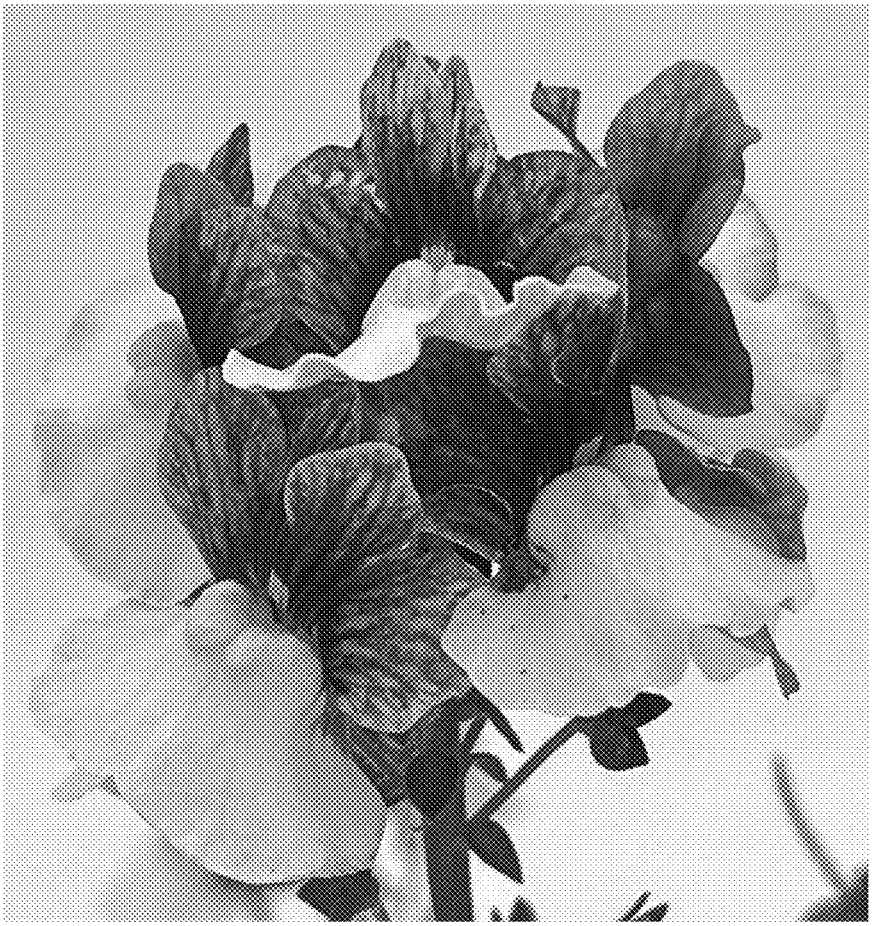

The photograph on the second sheet (FIG. 2) is a close-up view of a typical flowering plant of 'INNEMPLUHO'.

DETAILED BOTANICAL DESCRIPTION

The aforementioned photographs and following observations and measurements describe plants grown during the late summer to early autumn in 740-ml containers in a glass-covered greenhouse in Loudon, New Hampshire and under cultural practices typical of commercial *Nemesia* production. During the production of the plants, day temperatures ranged from 18° C. to 20° C. and night temperatures ranged from 16° C. to 18° C. Plants were pinched one time and were eight weeks from planting rooted young plants when the photographs and description were taken. In the following description, color references are made to The Royal Horticultural Society Colour Chart, 2015 Edition, except where general terms of ordinary dictionary significance are used.

Botanical classification: *Nemesia hybrida* 'INNEMPLUHO'.

Parentage:

*Female, or seed, parent*.—Proprietary selection of *Nemesia hybrida* identified as code name "purple white", not patented.

*Male, or pollen, parent*.—Proprietary selection of *Nemesia hybrida* identified as code number N 15 300-1 tet2, not patented.

Propagation:

*Type*.—By terminal vegetative cuttings.

*Time to initiate roots, summer*.—About ten days at temperatures about 20° C. to 25° C.

*Time to initiate roots, winter*.—About 14 to 18 days at temperatures about 18° C. to 20° C.

*Time to produce a rooted young plant, summer*.—About 14 to 20 days at temperatures about 20° C. to 33° C.

*Time to produce a rooted young plant, winter*.—About 14 to 20 days at temperatures about 18° C. to 20° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous annual; compact and upright to somewhat outwardly spreading plant habit; moderately vigorous to vigorous growth habit; moderate growth rate; freely branching habit with about eight to twelve primary branches with secondary laterals potentially developing at every node.

*Plant height*.—About 18 cm to 22 cm.

*Plant diameter*.—About 25 cm to 27 cm.

Lateral branch description:

*Length*.—About 22 cm to 24 cm.

*Diameter*.—About 3 mm.

*Internode length*.—About 1.5 cm.

*Strength*.—Moderately strong; flexible.

*Aspect*.—Mostly upright to somewhat outwardly and curving upright.

*Texture and luster*.—Longitudinally ridged; moderately pubescent, pubescence minute and fine; semi-glossy.

*Color, developing*.—Close to 144A.

*Color, developed*.—Close to 144A.

Leaf description:

*Arrangement*.—Opposite, simple; sessile.

*Length*.—About 3.75 cm to 4.25 cm.

*Width*.—About 1.5 cm to 1.75 cm.

*Shape*.—Lanceolate.

*Apex*.—Narrowly acute.

*Base*.—Obtuse.

*Margin*.—Dentate to serrate.

*Texture and luster, upper surface*.—Smooth, glabrous; glossy.

*Texture and luster, lower surface*.—Smooth, glabrous; matte.

*Venation pattern*.—Pinnate; arcuate.

*Color*.—Developing and fully expanded leaves, upper surface: Close to 147A; venation, close to 147A. Developing and fully expanded leaves, lower surface: Close to 147B; venation, close to 146A.

Flower description:

*Flower arrangement and habit*.—Bilabiate single flowers arranged in terminal and axillary racemes; flowers continually develop acropetally towards the apex; flowers face mostly outwardly; freely flowering habit with about 40 to 46 flowers per inflorescence and more than 1,000 flowers developing per plant during the flowering season.

*Fragrance*.—Moderate; floral, pleasant.

*Natural flowering season*.—Long flowering period, in New Hampshire, plants flower from spring until autumn; flowering continuous during this period; plants begin flowering about four weeks after planting rooted young plants.

*Flower longevity*.—Depending on temperature, flowers last about one week on the plant; petals not persistent, sepals persistent.

*Terminal inflorescence length*.—About 13 cm.

*Terminal inflorescence diameter*.—About 4 cm.

*Flower size*.—About 1.7 cm by 1.8 cm.

*Flower depth*.—About 1 cm.

*Flower buds*.—Length: About 5 mm. Diameter: About 3 mm. Shape: Ovoid. Texture and luster: Moderately pubescent; matte. Color, developing sepals: Close to 144A.

*Petals*.—Arrangement: Five petals; two upper and two lateral petals fused at base to form an upright lobed upper or banner lip; lower petal modified into a large recurved lower lip with convex oval protuberance and short nectar spur. Spur length: About 4 mm. Spur diameter, distally: About 1 mm. Spur texture and luster: Smooth, glabrous; matte. Spur color: Close to 144A strongly tinged with close to 71C. Lobe length: Upper petals: About 1 cm. Lateral petals: About 9 mm. Lower petal: About 8 mm. Lobe width: Upper petals: About 5 mm. Lateral petals: About 7 mm. Lower petal: About 1.8 cm. Shape: Upper and lateral petals: Obovate. Lower petal: Broadly bi-spatulate. Apex, upper and lateral petals: Broadly acute to obtuse. Apex, lower petal: Broadly obtuse and emarginate. Margin, upper and lateral petals: Entire; not undulate. Margin, lower petal: Entire, recurved and slightly undulate. Texture and luster, all petals, upper and lower surfaces: Smooth, glabrous; matte. Color, upper and lateral petals: When opening, upper surface: Close to 61A. When opening, lower surface: Close to 70A to 70B. Fully opened, upper surface: Close to N75A to N75B variably overlain with close to between 70A and 72A; small dot towards the throat, close to 8A to 8B; venation, close to between 70A and 72A; color does not change with subsequent development. Fully opened, lower surface: Close to N75A to N75B; venation, close to N75A to N75B; color does not change with subsequent development. Color, lower petal: When opening, upper surface: Close to 1B. When opening, lower surface: Close to 76A to 76B. Fully opened, upper surface: Close to between 5C and 6C; protuberance, close to 17B to 17C; venation, similar to lamina colors; colors dos not change with subsequent development. Fully opened, lower surface: Close to 76A to 76B; venation, similar to lamina colors; color does not change with subsequent development. Color, throat: Close to 17B to 17C.

*Sepals*.—Arrangement: Calyx star-shaped with five sepals fused at the base. Length: About 5 mm. Width: About 1 mm. Shape: Lanceolate. Apex: Acute. Margin: Entire. Texture and luster, upper and lower surfaces: Slightly to moderately pubescent; matte. Color, upper and lower surfaces: Close to 144A.

*Peduncles*.—Length: About 13 cm. Diameter: About 3.5 mm to 4.5 mm. Angle: Mostly upright to somewhat curving upwardly. Strength: Moderately strong; flexible. Texture and luster: Sparsely to moderately pubescent; longitudinally ridges; matte. Color: Close to 144A.

*Pedicels*.—Length: About 5 mm. Diameter: Less than 1 mm. Angle: About 30° to 45° degrees from peduncle axis. Strength: Moderately strong; wiry and flexible. Texture and luster: Smooth, glabrous; semi-glossy. Color: Close to 144A.

*Reproductive organs*.—Stamens: Quantity: Two per flower. Filament length: About 2.5 mm. Filament color: Close to 155D. Anther length: Less than 1 mm. Anther shape: Oblong. Anther color: Close to 17B to 17C. Pollen amount: None observed. Pistils: To date, pistil development has not been observed on plants of the new *Nemesia*; flowers are sterile.

*Seeds and fruits*.—To date, seed and fruit development have not been observed on plants of the new *Nemesia*.

Pathogen & pest resistance: To date, plants of the new *Nemesia* have not been observed to be resistant to pathogens and pests common to *Nemesia* plants.

Garden performance: Plants of the new *Nemesia* have been observed to have good summer garden performance and to tolerate wind and rain and temperatures ranging from about 5° C. to about 35° C.

It is claimed:

1. A new and distinct *Nemesia* plant named 'INNEMPLUHO' as herein illustrated and described.

* * * * *